(12) United States Patent
Wehling et al.

(10) Patent No.: US 8,313,784 B2
(45) Date of Patent: Nov. 20, 2012

(54) METHOD OF USING GUAVA EXTRACT

(75) Inventors: Fred Wehling, Greenfield, MN (US);
Mary Aldritt, Excelsior, MN (US);
GeMing Lui, Honolulu, HI (US)

(73) Assignee: Amerilab Technologies, Inc., Plymouth, MN (US)

( * ) Notice: Subject to any disclaimer, the term of this patent is extended or adjusted under 35 U.S.C. 154(b) by 0 days.

(21) Appl. No.: 13/011,516

(22) Filed: Jan. 21, 2011

(65) Prior Publication Data
US 2011/0117217 A1   May 19, 2011

Related U.S. Application Data

(63) Continuation of application No. 12/170,972, filed on Jul. 10, 2008, now abandoned, and a continuation-in-part of application No. 11/327,586, filed on Jan. 6, 2006, now Pat. No. 7,611,739.

(51) Int. Cl.
*A61K 36/00* (2006.01)
*A61K 36/258* (2006.01)

(52) U.S. Cl. .......... 424/774; 424/725; 424/728; 514/52; 514/175

(58) Field of Classification Search .................. None
See application file for complete search history.

(56) References Cited

U.S. PATENT DOCUMENTS

| | | | |
|---|---|---|---|
| 5,942,231 A | 8/1999 | Hamada et al. | |
| 5,955,057 A | 9/1999 | Maunder et al. | |
| 5,962,022 A | 10/1999 | Bolt et al. | |
| 5,972,916 A | 10/1999 | Armellino et al. | |
| 6,171,633 B1 | 1/2001 | Dulebohn et al. | |
| 6,616,950 B2 | 9/2003 | Pushpangadan et al. | |
| 6,811,793 B2 | 11/2004 | Wehling | |
| 6,824,798 B2 | 11/2004 | Koenig et al. | |
| 2002/0172738 A1 | 11/2002 | Young | |
| 2002/0187219 A1* | 12/2002 | Yang et al. ................. | 426/72 |
| 2003/0124208 A1 | 7/2003 | Makino et al. | |

FOREIGN PATENT DOCUMENTS

| | | |
|---|---|---|
| CN | 1548142 | 11/2004 |
| EP | 1245234 | 10/2002 |
| IN | 2004DE02352 | 3/2005 |
| JP | 60054665 | 3/1985 |
| JP | 08099893 | 4/1996 |
| JP | 09012465 | 1/1997 |
| JP | 09227393 | 9/1997 |
| JP | 2001039884 | 2/2001 |
| JP | 2001226274 | 8/2001 |
| JP | 2002255837 | 9/2002 |
| JP | 2003189828 | 7/2003 |
| JP | 2004267075 | 9/2004 |
| JP | 2004075571 | 11/2004 |
| KR | 20020094087 | 12/2002 |
| KR | 20030026939 | 4/2003 |
| KR | 20040066768 | 7/2004 |
| WO | WO 01/013742 | 3/2001 |

OTHER PUBLICATIONS http://www.mayoclinic.com/health/diabetes/DS01121/METHOD=print&DSECTION=all—accessed Dec. 2011.*

Das, A., T. Sen, A.S. Dutta, and A.K. Nag Chaudhuri. 1994. "Preliminary studies on the anti-inflammatory activity of the mechanolic fraction of *Psidium guajava* Linn. fruit extract." *Indian Journal of Pharm. Sci.* 56:4:163.

Dhara, A.K., B. Gebremariam, and A.K. Hag Chowdhury. 1994. "Neuropharmacological evaluation of *Psidium guajava* fruit extract." *Indian J. Pharm. Sci.* 56:4:164.

Garcia, E.A. Conde, V.T. Nascimento, and A.B. Santiago Santos. 2003. "Inotropic effects of extracts of *sidium guajava* L. (guava) leaves on the guinea pig atrium." *Brazilian Journal of Medical and Biological Research*. 36:5:661-68.

Jaiarj, Pranee, et al., "Anticough and antimicrobial activities of *Psidium guajava* Linn. Leaf extract," J. of Ethnopharmacology, 1999, vol. 67, pp. 203-212.

Kavimani, S., R. Ilango Karpagam, and B. Jaykar. 1997. "Anti-inflammatory activity of volatile oil of *Psidium guajava*." *Indian Journal of Pharm. Sci*. 59:3:142-44.

Lutterodt, G.D. 1994. "Effect on electrolyte and water transport by *Psidium gaujava* extract in a rat secretory diarrhoea model." *Asia Pacific Journal of Pharmacology*. 9:3:189-93.

Lutterodt, G. 1989. "Inhibition of gastrointestinal release of acetylcholine by quercetin as a possible mode of action of *Psidium guajava* leaf extracts in the treatment of acute diarrheal disease." *Journal of Ethnopharmacology*. 25:3:235-248.

Lutterodt, G.D. 1992. "Inhibition of Microlax-induced experimental diarrhea with narcotic-like extracts of *Psidium guajava* leaf in rats." *Journal of Ethnopharmacology*. 37:2:151-57.

Lutterodt, G. and A. Maleque. 1988. "Effects on mice locomotor activity of a narcotic-like principle from *Psidium guajava* leaves." *Journal of Ethnopharmacology*. 24:23:219-232.

Maruyama, Y., H. Matsuda, R. Matsuda, M. Kuo, T. Hatano, and T. Okuda. 1985. "Study on *Psidium guajava* l. anti-diabetic effect and effective components of the leaf of *Psidium guajava* Part 1." *Shoyakugaku Zasshi*. 39:4:261-269.

Mukhtar, H.M., S.H. Ansari, M. Ali, T. Naved, and Z.A. Bhat 2004. "Anti-hyperglycemic activity of *Psidium gaujava* bark extract" *Journal of Natural Remedies*. 4:2:150-54.

Mukhtar, H.M., S.H. Ansari, M. Ali, T. Naved, and Z.A. Bhat. 2004. "Effect of water extract of *Psidium guajava* leaves on alloxan-induced diabetic rats." *Pharmazie*. 59:9:734-35.

Mukhtar, H.M. ,S.H. Ansari, M. Ali, T. Naved, and Z.A. Bhat. 2004. "Hypoglycemic activity of *Psidium guajava* Linn. Leaf extract." *Journal of Natural Remedies*. 4:2:186-89.

Obasi, B.N.B., C.A. Igboechi, D.C. Anuforo, and K.N. Aimufua, 1993. "Effects of extracts of *Newbouldia laevis*, *Psidium guajava* and *Phyllanthus amarus* on gastrointestinal tract." *Fitoterapia*. 64:3:235-38.

(Continued)

*Primary Examiner* — Susan Hoffman

(74) *Attorney, Agent, or Firm* — Allison Johnson; Allison Johnson, P.A.

(57) ABSTRACT

A method of using guava extract is disclosed that includes administering guava extract to a mammal to inhibit, prevent or alleviate at least one of a headache, nausea, dry mouth, lack of appetite, shakiness, and fatigue. A composition is also disclosed that includes a pharmaceutically acceptable carrier and guava extract.

10 Claims, No Drawings

OTHER PUBLICATIONS

Olajide, O.A., S.O. Awe, and J.M. Makinde. 1999. "Pharmacological studies on the leaf of *Psidium guajava*." *Fitoterapia*. 70:1:25-31.

Oh, W.K., C.H. Lee, M.S. Lee et al. 2005. "Antidiabetic effects from *Psidium guajava*." *Journal of Ethnopharmacology*. 96:3:411-15.

Pittler, Max H., et al., "Effectiveness of artichoke extract in preventing alcohol-induced hangovers: a randomized controlled trial," *Canadian Medical Association Journal*, Dec. 8, 2003, pp. 1269-1273, vol. 169 No. 12, Canada.

Razak, Fathilah Abdul, et al., "The anti-adherence effect of Piper beetle and *Psidium guajava* extracts on the adhesion of early settlers in dental plaque to saliva-coated glass surfaces," *Journal of Oral Science*, Dec. 2003, vol. 45 No. 4, pp. 201-206, Japan, Database Medline, U.S. National Library of Medicine, Bethesda, MD, US.

Sanches, N.R., D.A. Garcia Cortez, M.S. Schiavini, C.V. Nakamuar, and B.P. Dias Filho. 2005. "An evaluation of antibacterial activities of *Psidium gaujava* (L.)." *Brazilian Archives of Biology and Technology*. 48:3:429-36.

Somchit, M.N., M.R. Sulaiman, Z. Ahjmad, D.A. Israf, and H. Hosni. 2004. "Non-opoid anti-nociceptive effect of *Psidium gaujava* leaves extract." *Journal of Natural Remedies*. 4:2:174-78.

Taylor, Leslie, "GUAVA (*Psidium guajava*)," Raintree Nutrition, Tropical Plant Database, Dec. 29, 2005, pp. 1-8, http://web.archive.org/web/20051229045356/http://rain-tree.com/guava.htm.

Wiese, J., et al., "Effect of *Opuntia ficus* indica on symptoms of the alcohol hangover," Archives of Internal Medicine, Jun. 28, 2004, pp. 1334-1340, vol. 164, United States.

Xu, B.J., et al., "Natural medicines for alcoholism treatment: a review," *Drug and Alcohol Review*, Nov. 2005, pp. 525-536, vol. 24 No. 6.

Yamashiro, S., K. Noguchi, M. Tohsihiro, et al. 2003. "Cardioprotective effects of extracts from *Psidium guajavea* L. and Limonium wrightii, Okinawan medicinal plants, against ischemia-reperfusion injury in perfused rat hearts." Pharmacology (Basel). 67:3:128-135.

Kulkarni, A.R., "Screening of Guava Leaves Extracts for Analgesic, Antiinflammatory and antiulcer activity in albino rats," *Indian Drugs*, Jun. 1999, pp. 363-367, vol. 36, No. 6, India.

Gutierrez, R.M.P., et al., "*Psidium guajava*: A review of its traditional uses, phytochemistry and pharmacology," *Journal of Ethnopharmacology*, (available online Feb. 3, 2008), pp. 1-27, vol. 117, Elsevier Ireland Ltd.

Lutterodt, G.D., "Analgesic Efficacy of *Psidium Guajava* Extractive in Mouse Experimental Pain Models," *Asia Pacific J. of Pharmacology*, 1993; 8: 83-87 (1993).

Lieberman, et al., eds., *Pharmaceutical Dosage Forms: Tablets*, Second Ed., vol. 1, pp. 285-289, 291-294, 298-300, and 302-303, 1989.

Lozoya, Xavier, et al., "Intestinal anti-spasmodic effect of a phytodrug of *Psidium guajava* folia in the treatment of acute diarrheic disease," J. of Ethnopharmacology, 2002, vol. 83, pp. 19-24.

Mohammed Azam Khan, Muheet-e-Azam, vol. I , Matba Nizami, Kanpur, India 1896.

Mohammed Najmul Ghani Khan, Khazaain-al-Advia, vol. I, p. 573, Nadeem Yunus Printer/Sheikh Mohd Basheer & Sons, Lahore, Pakistan, 1911.

\* cited by examiner

METHOD OF USING GUAVA EXTRACT

CROSS-REFERENCE TO RELATED APPLICATIONS

This application is a continuation of U.S. Ser. No. 12/170,972, filed on Jul. 10, 2008, now abandoned which is a continuation-in-part of U.S. application Ser. No. 11/327,586, filed on Jan. 6, 2006, now U.S. Pat. No. 7,611,739, both of which are incorporated herein.

BACKGROUND

The invention relates to administering guava extract.

The guava plant, *psidium guajava L*., has been used as a source of nutrition by many cultures; its fruit is eaten as is, made into juices and jellies, and used in other food products. Parts of the guava plant have been used by various cultures to treat diarrhea and sore gums. The guava plant has also been studied to ascertain its effects on various conditions of the human body including diabetes and obesity.

Human beings have been consuming alcohol, in the form of ethanol, for centuries. After alcohol is ingested it is absorbed from the stomach and upper gastrointestinal tract. Alcohol that a person drinks shows up in the person's breath because it is absorbed from the mouth, throat, stomach and intestines into the bloodstream. Alcohol is not chemically changed while in the bloodstream. As the blood passes through the lungs, some of the alcohol moves across the membranes of the lung's air sacs (alveoli) into the air, because alcohol is volatile. The concentration of the alcohol in the alveolar air is related to the concentration of the alcohol in the blood. By analyzing the breath of an individual, one can determine the level of alcohol in the individual. Although alcohol is found in human breath whether or not an individual has been consuming it, in most circumstances the only possible way to increase the level of alcohol in the body to a point sufficient to cause behavioral impairment is to ingest alcohol.

Blood Alcohol Content, which is also referred to as Blood Alcohol Concentration, (both of which are referred to as "BAC") can be determined by breath analysis for the volatile organic compound ethanol. BAC is a measure of the mass of alcohol (i.e., ethanol) in a given volume of blood and is reported in milligrams (mg) ethanol per 100 milliliters (mL) blood. A BAC measurement of 0.04%, for example, translates to a concentration of 40 mg of alcohol in 100 mL of blood. Breath analysis alcohol content (BrAC) in the United States is specified as BAC/2100. At 34° C. (i.e., 93° F.) ethanol is in equilibrium in blood at a ratio of roughly 2100:1 based on the distribution of ethanol in equilibrium with the blood in the deep part of the lungs. In other words, 2100 ml of air in the deep parts of the lungs contain the same amount of ethanol that is present in 1 ml of blood. Because the ethanol concentration in the breath is related to that in the blood, the BAC can be calculated from the breath alcohol measurement. The ratio of breath alcohol to blood alcohol is 2,100:1. This means that 2,100 milliliters (ml) of alveolar air will contain the same amount of alcohol as 1 ml of blood.

Consuming too much alcohol can cause a variety of negative effects in the body including impairing motor skills and reaction times. When people who have consumed too much alcohol operate a motor vehicle, they can pose a danger to themselves and other motorists. As a result, legal standards for permissible blood alcohol content for operating a motor vehicle have been developed. For many years, the legal standard for permissible blood alcohol content across the United States was a BAC measurement of 0.10%, but many states have now adopted the 0.08% standard. The federal government has pushed states to lower the legal limit. The American Medical Association takes the position that a person can become impaired when the blood alcohol level hits 0.05%.

Consuming too much alcohol can also result in a hangover, which is often accompanied by a variety of symptoms including at least one of headache, nausea, lack of appetite, shakiness, fatigue, dry mouth, an overall feeling of being unwell, and decreased occupational, cognitive, or visual-spatial skill performance. The negative effects of alcohol consumption are due in large part to the toxic effects of acetaldehyde. Although a portion of the alcohol is eliminated in urine and breath, a majority of the alcohol is oxidized, primarily in the liver. The liver converts ethanol to acetaldehyde by alcohol dehydrogenases. Acetaldehyde is processed by the liver at a fixed rate, regardless of how much alcohol is in the bloodstream. Acetaldehyde is then oxidized to acetic acid by acetaldehyde dehydrogenases, which is rapidly metabolized to carbon dioxide and water.

Acetaldehyde provokes disturbances in bodily processes by, for example, forming adducts with hemoglobin and proteins of plasma of the brain and other organs, and inhibiting the transfer of reducing agents along the mitochondrial respiratory chain. Acetaldehyde also accumulates in the cerebellum causing headache by contracting cerebral blood vessels thereby decreasing blood flow resulting in pain.

SUMMARY

In one aspect, the invention features a method of using guava extract that includes administering guava extract to a mammal (including, e.g., a human being, a chimp, a monkey, a dog, a pig, a rat, and a mouse). In some embodiments, the method includes administering guava extract to a mammal experiencing a feeling that includes at least one of headache, nausea, dry mouth, lack of appetite, shakiness, and fatigue to alleviate, inhibit or prevent the feeling. In other embodiments, the method includes administering guava extract to a mammal at a time sufficient to alleviate, inhibit or prevent a feeling that includes at least one of headache, nausea, dry mouth, lack of appetite, shakiness, and fatigue. In other embodiments, the method includes administering at least 500 mg of guava extract to a mammal to prevent a feeling that includes at least one of headache, nausea, dry mouth, lack of appetite, shakiness, and fatigue.

In another aspect, the invention features a method of using guava extract that includes administering guava extract to a human within no greater than 24 hours of the human feeling a headache. In one embodiment, the administering of guava extract occurs prior to said human feeling a headache. In another embodiment, the administering of guava extract occurs within about 1 hour of the human feeling a headache.

In other embodiments, the method includes administering guava extract to a human at a time and in an amount sufficient to alleviate a feeling of a headache in the human.

In some embodiments, the method includes administering guava extract to a human who expects to feel a headache.

In one embodiment, the method includes treating a mammal having an elevated (i.e., greater than normal due to alcohol consumption) blood alcohol content by administering guava extract to the mammal. In another embodiment, administering the guava extract includes administering an amount of guava extract sufficient to decrease the blood alcohol content of the mammal. In some embodiments, the mammal has a blood alcohol content of at least 0.05% prior to the administering. In other embodiments, the administering includes administering at least 250 mg of guava extract to the mammal.

In some embodiments, the administering includes administering at least 500 mg, at least about 1000 mg, at least about 1500 mg, or even at least about 2000 mg of guava extract to the mammal.

In another embodiment, the administering includes administering guava extract in an amount sufficient to decrease the blood alcohol content of the mammal by at least about 20%. In other embodiments, the administering includes administering guava extract in an amount sufficient to decrease the blood alcohol content of the mammal by at least 0.02 units.

In another aspect, the invention features a method of decreasing the aldehyde content in a mammal experiencing elevated levels of aldehyde by administering guava extract to the mammal. In some embodiments, the administering includes administering at least 500 mg, at least about 1000 mg, at least about 1500 mg, or even at least about 2000 mg of guava extract to the mammal. In one embodiment, the method inhibits, alleviates or prevents the feelings associated with a hangover.

In other aspects, the invention features a the method of using guava extract includes administering alcohol to a mammal and administering guava extract within no greater than about 12 hours of the administering of the alcohol. In one embodiment, the administering guava extract occurs within about 1 hour of the administering alcohol. In another embodiment, the guava extract includes a water-soluble extract of guava leaves. In other embodiments, the guava extract includes at least one of an organic solvent soluble extract of guava leaves and an oil soluble extract of guava leaves.

In some embodiments, the administering guava extract occurs prior to the consuming alcohol.

In other embodiments of the methods disclosed herein, the administering includes administering least 250 mg, at least 500 mg, at least about 1000 mg, at least about 1500 mg, or even at least about 2000 mg of guava extract to the mammal.

In another aspect, the invention features a composition that includes at least 500 mg guava extract and a pharmaceutically acceptable carrier. In one embodiment, the carrier includes water, oil, binder, lubricant, or a combination thereof. In other embodiments, the carrier includes an aqueous liquid that includes carbonation.

In some embodiments, a composition disclosed herein is a formulation in the form of a powder, liquid, tablet, pill, capsule, gel cap, a chewing gum or a combination thereof.

In another embodiment, a composition disclosed herein is a formulation in the form of a suspension, a solution, an emulsion, a syrup or a combination thereof.

In one embodiment, the composition is a solid effervescent composition that includes at least 500 mg guava extract and a pharmaceutically acceptable carrier that includes an effervescent agent that includes an acid and a base. In some embodiments, the composition is in the form of a tablet and the carrier further that includes from 10% by weight to about 60% by weight binder and from 1% by weight to about 15% by weight lubricant. In some embodiments, the composition further includes an ice tea flavor agent, FD&C red dye number 40 or a combination thereof.

In other embodiments, the formulation is in the form of chewing gum and the carrier further includes a gum base that includes a water-soluble bulk portion, and a water-insoluble chewable gum base portion.

In some embodiments of the methods disclosed herein, the administering includes administering at least 500 mg, at least about 1000 mg, at least about 1500 mg, or even at least about 2000 mg of guava extract to the mammal.

The guava extract is provided in an easy to ingest dosage form that is palatable and is relatively quick acting. In some cases the guava extract alleviates the effects of a hangover including improving at least one of the overall feeling of the mammal, headache, nausea, dry mouth, lack of appetite, shakiness, and fatigue. In some cases the guava extract reduces the breath alcohol content of a mammal, the aldehyde content in a mammal, at least one negative physical feeling associated with a hangover or a combination thereof.

Other features and advantages will be apparent from the following description of the preferred embodiments and from the claims.

GLOSSARY

In reference to the invention, these terms have the meanings set forth below:

As used herein the term "an effective amount of guava extract" means an amount that causes a decrease in the amount of alcohol expired through the lungs based on the measured breath alcohol content, a decrease in the level of alcohol in the blood, a decrease in aldehyde content, or a combination thereof.

As used herein, the term "unit dose" or "unit dosage" refers to physically discrete units that contain a predetermined quantity of active ingredient calculated to produce a desired therapeutic effect.

As used herein the term "oral dosage form" is used in a general sense to reference a product that is administered orally.

As used herein the term "carrier" means a substance used in association with guava extract for aiding in the administration of guava extract.

The term "pharmaceutically acceptable" when used herein as an adjective, means substantially non-toxic and substantially non-deleterious to the recipient.

DETAILED DESCRIPTION

The method includes administering (e.g., administering to others or to one's self including, e.g., ingesting)) guava extract to a mammal before, during or after consumption of alcohol, feeling the effects of a hangover, feeling a headache, nausea, dry mouth, lack of appetite, shakiness, fatigue or a combination thereof, and combinations thereof. Preferably the guava extract is administered at a time and provided in an amount sufficient to alleviate at least one of dehydration, headache, nausea, lack of appetite, shakiness, fatigue, dry mouth, and an overall feeling of being unwell.

On method of administering guava extract includes administering guava extract in an amount sufficient to reduce the mammal's blood alcohol content, breath alcohol content, aldehyde (e.g., formaldehyde, acetaldehyde and combinations thereof) content, or a combination thereof. The guava extract is preferably administered in an amount and at a time sufficient to decrease the blood alcohol content of the mammal by at least about 10%, by at least about 20%, or even by at least about 30%, by at least 0.02 units, by at least 0.03 units, or even by at least 0.05 units as measured based on breath alcohol content.

The guava extract can be administered at any suitable time including, e.g., within no greater than 24 hours, no greater than 12 hours, no greater than 5 hours, no greater than 3 hours, no greater than 2 hours, no greater than 1 hour, no greater than 0.5 hour, just after or before, or even simultaneously while consuming alcohol. Alternatively or in addition, the guava extract can be administered to a mammal that is feeling the effects of a hangover or expects to feel the effects of a hangover at any suitable time including, e.g., within no greater than 24 hours, no greater than 12 hours, no greater than 5 hours, no greater than 3 hours, no greater than 2 hours, no greater than 1 hour, no greater than 0.5 hour, after, before, or even simultaneously with the feelings of a hangover.

Alternatively or in addition, the guava extract can be administered to a mammal having a blood alcohol content of at least 0.03%, at least 0.04%, at least 0.05%, at least 0.06%, at least 0.08%, at least 0.1% or even greater than 0.15%.

Alternatively or in addition, the guava extract is administered to a mammal that is feeling a headache, nausea, dry mouth, lack of appetite, shakiness, fatigue or a combination thereof, or expects to feel the aforementioned feelings, at any suitable time including, e.g., within no greater than 24 hours, no greater than 12 hours, no greater than 5 hours, no greater than 3 hours, no greater than 2 hours, no greater than 1 hour, no greater than 0.5 hour, after, before, or even simultaneously with experiencing at least one of the aforementioned feelings. Guava extract also can be administered on a daily basis to alleviate, prevent or inhibit the occurrence of a headache.

The effective amount of guava extract will vary depending on a number of factors including, e.g., the physical characteristics of the individual (e.g., height, weight, age, and physical health), the purpose for which the guava extract is being administered (e.g., to decrease blood alcohol content, to alleviate, prevent or inhibit a feeling (e.g., headache, nausea, dry mouth, lack of appetite, shakiness, or fatigue, and combinations thereof), the amount of alcohol consumed or to be consumed by the individual, the type and severity of the feeling (e.g., headache, nausea, dry mouth, lack of appetite, shakiness, fatigue, and combinations thereof) the means used to administer the dosage, and combinations thereof.

The guava extract is preferably provided in a unit dosage form and can be administered in a single dose or in multiple doses. The effective dose for a given individual is usually set by the judgment of the individual. The guava extract is generally effective over a wide dosage range. Amounts that have been found to be useful include at least about 100 mg guava extract per dose, at least about 250 mg/dose, at least about 500 mg/dose, at least about 800 mg/dose, at least about 1000 mg/dose, at least about 1500 mg/dose, at least about 2000 mg/dose, at least about 3000 mg/dose, at least about 5000 mg/dose, or even at least about 10,000 mg/dose.

The dose of guava extract can be administered on any suitable basis including, e.g., at least once a day, at least twice a day, at least three times a day, at least four times a day, or even at least five times a day and at various intervals. Multiple doses can also be given during each dosing including, e.g., at least two 100 mg doses at least once a day, at least twice a day, or even at least five times a day, or even at least two 250 mg tablets at least once a day.

The dose of guava extract can include neat guava extract, i.e., the dose is free of other components, or it can include components in addition to guava extract including, e.g., a variety of carriers. The dose preferably includes from 0.1% to 100% by weight, at least about 10% by weight, at least about 20% by weight, at least about 25% by weight, at least about 30% by weight, at least about 40% by weight guava extract.

Useful sources of guava extract include extracts of various parts of the plant *psidium guajava L.* including the fruit, leaves, stems, and roots thereof. Preferably the guava extract is obtained from guava leaves. The guava extract can be obtained through a solvent extraction process wherein at least a portion of the guava plant is contacted with a liquid including, e.g., an organic solvent (e.g., methanol, ethanol, butanol and isopropanol), water (e.g., tap water, room temperature water, elevated temperature water (e.g., boiling water) and combinations thereof), oil (e.g., mineral oil, elevated temperature oil, vegetable oils, animal oils and combinations thereof), and combinations thereof. The resulting extract is then gathered for use. The guava plant or a portion thereof can also be treated prior to extraction. Useful treatments include, e.g., drying, lyophilizing, freeze drying, humidifying, and combinations thereof.

Useful carriers for the guava extract include, e.g., excipients, diluents, binders, lubricants, disintegrants, coloring agents, sweetening agents, and combinations thereof including, e.g., carbohydrates, waxes, water soluble and/or swellable polymers, hydrophilic materials, hydrophobic materials, gelatin, oils, organic solvents, water, and combinations thereof. The selection of the carrier will depend upon the means by which the guava extract is to be administered.

The dose of guava extract can optionally include wetting agents, lubricating agents, emulsifiers, suspending agents, preservatives, sweeteners, stabilizers, flavoring agents, coloring agents, and combinations thereof, useful examples of which are set forth below.

The dose of guava extract can be provided in a variety of packages including metal foil pouches, tubes (e.g., plastic and metal tubes), ampoules, in multidose containers. The packaging preferably is air tight and impermeable to moisture.

The dose of guava extract can be administered in any convenient manner including, e.g., by oral, intravenous, subcutaneous, intramuscular and subcutaneous routes, and combinations thereof. Oral administration can be by any suitable dosage form including, e.g., powder (e.g., effervescent powders, and powdered drink mixes), tablet (e.g., quick dissolve tablets), granulations (e.g., effervescent granulations, chewable granulations), pill, capsule, gel caps, composite (e.g., a layered tablet construction, a construction that includes a continuous phase and a discontinuous phase), chewable dosage forms including chewing gum and chewable tablets, wafer (e.g., disintegrating tablets and dissolving tablets), and liquid formulations (e.g., solutions and dispersions), e.g., beverages, e.g., canned and bottled beverage, a dry or liquid aerosol that can be inhaled or sprayed, and combinations thereof. The guava extract can be provided in the form of a sterile solution by direct injection into the bloodstream of the individual to be treated. The guava extract is preferably formulated into a dosage form that provides an easily controllable dose of guava extract, is easy to ingest, and is easy to handle.

One example of a useful solid effervescent composition for guava extract includes guava extract and an effervescent agent that includes an acid and a base. The guava extract is preferably dried and sieved to a suitable particle size (e.g., using a number 12 sieve) prior to combining with the other ingredients of the effervescent composition. The effervescent composition preferably includes guava extract in an amount of at least about 250 mg, at least about 500 mg, at least about 800 mg, at least about 1000 mg, at least about 1500 mg, or even at least about 2000 mg.

The effervescent agent is activated when contacted with an aqueous liquid, e.g., water (e.g., when the powder or tablet is placed in a glass of water). The water liberates the acid and base and enables the acid and base to react with each other to produce carbon dioxide gas, which imparts carbonation to the aqueous composition. Examples of useful acids include citric acid, ascorbic acid, aspartic acid, malic acid, adipic acid, tartaric acid, fumaric acid, succinic acid, sodium acid pyrophosphate, lactic acid, hexamic acid, amino acids, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. Preferably acid is present in the effervescent composition in an amount of from 10% by weight to about 60% by weight, from about 15% by weight to about 50% by weight, or even from about 25% by weight to about 40% by weight.

The base preferably is capable of generating a gas such as carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide, amino acid carbonates, and mixtures thereof. The effervescent composition preferably includes base in an amount of from 10% by weight to about 60% by weight, from about 15% by weight to about 50% by weight, or even from about 25% by weight to about 40% by weight.

The effervescent composition can optionally include a variety of additional active agents including, e.g., vitamins, amino acids, pharmaceutical agents, minerals, dietary supplements, and combinations thereof. Suitable vitamins include, e.g., ascorbic acid (vitamin C), aspartic acid, thiamin, riboflavin, nicotinic acid, pantothenic acid, pyridoxine, biotin, folic acid, niacin, vitaminB12, lipoic acid, vitamin A, vitamin D, vitamin E and vitamin K and coenzymes thereof, choline, carnitine, and alpha, beta, and gamma carotenes. Examples of coenzymes include thiamine pyrophosphates, flavin mononucleotide, flavin adenine dinucleotide, nicotinamide adenine dinucleotide, nicotinamide adenine dinucleotide phosphate coenzyme A pyridoxal phosphate, biocytin, tetrahydrofolic acid, coenzyme B12, lipoyllysine, 11-cis-retinal, and 1,25-dihydroxycholecalciferol and mixtures.

Suitable amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and mixtures thereof.

Examples of minerals include iron, zinc, selenium, copper, iodine, phosphorus, chromium and mixtures thereof.

Suitable dietary supplements include, e.g., bee pollen, bran, wheat germ, kelp, cod liver oil, ginseng, and fish oils, amino-acids, proteins, vitamins, minerals alpha-glycerylphosphorylcholine, acetyl-L-carnitine and salts thereof, docosahexaenoic acid, cranberry extract, chondroitin, methylsulfonylmethane, and mixtures thereof.

The effervescent composition can also include other ingredients including, e.g., flavor agents, fillers, surfactants (e.g., polysorbate 80 and sodium lauryl sulfate), color agents including, e.g., dyes and pigments, sweeteners, and flow agents.

Useful flavor agents include natural and artificial flavor agents including, e.g., volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors, ice tea flavoring, and combinations thereof. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin), and mixtures thereof. Preferably the effervescent composition includes at least about 100 mg, at least about 200 mg, no greater than about 500 mg or even no greater than about 400 mg flavor agent.

Useful color agents include, e.g., food, drug and cosmetic (FD&C) colors including, e.g., dyes (e.g., FD&C red no. 40), lakes, and certain natural and derived colorants. Useful lakes include dyes absorbed on aluminum hydroxide and other suitable carriers.

Useful sweetening agents include stevia, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

The solid effervescent composition can be provided in a variety of forms including, e.g., powder, granulation, tablet, capsule, pellet and composite. Preferred effervescent tablets have a hardness of at least 3 kilopounds (Kp), preferably at least 5 Kp, from about 5 Kp to about 10 Kp, or even from about 5 Kp to about 8 Kp, as measured on a standard hardness tester fitted with a strain gauge.

When in the form of a tablet, the effervescent composition preferably also includes binder, lubricant, and combinations thereof. Examples of suitable binders include, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof. Preferably the binder is water soluble.

Where present, the binder of the effervescent composition is present in an amount sufficient to assist in holding the components of the composition together in the form of a tablet. When present, the composition preferably includes binder in an amount from 10% by weight to about 60% by weight, from about 15% by weight to about 50% by weight, or even from about 20% by weight to about 40% by weight, or even 20% by weight to 30% by weight.

Various lubricants are suitable for use in the effervescent composition including water dispersible, water soluble, water insoluble lubricants and combinations thereof. Preferred lubricants are water soluble. Some lubricants also provide a binder function and vice versa. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof.

The effervescent composition preferably includes a sufficient amount of lubricant to enable the composition to be formed into tablets and released from a high speed tableting press in the form of a tablet. When present, the composition preferably includes lubricant in an amount of from 1% by weight to about 15% by weight, from about 1% by weight to about 12% by weight, from about 2% by weight to about 10% by weight, or even from about 3% by weight to about 8% by weight.

The components of the effervescent composition are preferably dried and sieved as necessary prior to formulating.

The effervescent composition is preferably stored in a moisture-proof package including, e.g., sealed metal foil pouches, blister packs, and desiccant capped tubes. Useful packaging materials further include metal foil, plastic films, and blister packaging.

The effervescent composition can be administered by adding the composition to excess water or vice versa, e.g., an eight ounce glass of tap water, to form an aqueous composition, followed by ingestion. After addition of the effervescent composition to an aqueous liquid, the composition optionally can be stirred to facilitate dispersion and/or dissolution of the composition in the aqueous liquid.

The effervescent composition for tableting is well suited to the mass production of effervescent tablets that are free from picking, die wall etching, capping and lamination. Any suitable tablet mass production equipment and processes can be used. Examples of useful tableting processes for effervescent compositions are described in Pharmaceutical Dosage Forms, Vol. 1, (Herbert A. Lieberman et al. eds, $2^{nd}$ ed. 1989) and incorporated herein. The tablets can then be manufactured in an automated process in which multiple dies of a tablet press are filled sequentially or simultaneously with the effervescent composition, two punches compress the effervescent composition to form the tablet(s), and then the tablet(s) is ejected from the die. The tablet is then placed in packaging material, which is then sealed to form an air tight sealed package. The packaged tablet can be further processed by conveying it to other processing stations including, e.g., additional packaging stations for further packaging, e.g., boxing and bagging.

The tablet manufacturing and initial packing operations are preferably performed in a controlled environment in which the temperature and humidity are controlled. Preferably the controlled environment has less than 18 grains, less than 16 grains, or even less than 15 grains of moisture.

Other useful methods of making effervescent tablets, as well as coated tablets, sustained release tablets, coated particles, and chewable tablets, are disclosed in Pharmaceutical Dosage Forms, Vols. 1-3, (Lieberman et al. eds. $2^d$ ed. 1989) and incorporated herein. A useful method of making quick dissolve tablets is disclosed in U.S. Pat. No. 6,368,625 and incorporated herein.

One example of a suitable chewing gum formulation includes guava extract and a chewing gum base. A useful chewing gum base includes a water-soluble bulk portion, a water-insoluble chewable gum base portion, and, optionally, a flavor agent. The water-soluble portion dissipates with a portion of the flavoring agent over a period of time during chewing. The gum base portion is retained in the mouth throughout the chew. Useful water-insoluble gum bases include, e.g., elastomers, resins, fats, oils, softeners, inorganic fillers, and combinations thereof. The water-insoluble gum base may optionally include wax. The chewing gum preferably includes from about 5% by weight to about 95% by weight, from about 10% by weight to about 50% by weight, or even from about 25% by weight to about 35% by weight water-insoluble gum base.

An example of a useful water-insoluble gum base includes from about 20% by weight to about 60% by weight synthetic elastomer, from about 0% by weight to about 30% by weight natural elastomer, from about 5% by weight to about 55% by weight plasticizer, from about 4% by weight to about 35% by weight filler, from about 5% to about 35% by weight softener, and optionally minor amounts (i.e., no greater than about 1% by weight) of additives including, e.g., coloring agents, antioxidants, flavor agents, and combinations thereof.

Useful synthetic elastomers include, e.g., polyisobutylene (e.g., polyisobutylene having a weight average molecular weight of from about 10,000 to about 95,000, or even from about 50,000 to 80,000), isobutylene-isoprene copolymer (butyl elastomer), styrene-butadiene, copolymers of styrene-butadiene wherein the styrene to butadiene ratio is from about 1:3 to about 3:1, or even from about 1:1 to about 1:3, polyvinyl acetate (e.g., polyvinyl acetate having a weight average molecular weight of from about 2,000 to about 90,000, or even from about 10,000 to about 65,000), polyisoprene, polyethylene, vinyl acetate-vinyl laurate copolymers (e.g., vinyl laurate copolymers having a vinyl laurate content from about 5% by weight to about 50% by weight, or even from about 10% by weight to about 45% by weight), and combinations thereof.

Useful natural elastomers include, e.g., natural rubber (e.g., smoked latex, liquid latex, and guayule), natural gums (e.g., jelutong, lechi caspi, perillo, sorva, massaranduba balata, massaranduba chocolate, nispero, rosindinha, chicle, gutta hang kang, and combinations thereof), and combinations thereof.

Useful elastomer plasticizers include, e.g., natural rosin esters (e.g., glycerol esters of partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin), synthetic plasticizers including, e.g., terpene resins derived from alpha-pinene, beta-pinene, d-limonene, and combinations thereof, and combinations thereof.

Useful fillers and texturizers include, e.g., magnesium carbonate, calcium carbonate, ground limestone, silicates (e.g., magnesium silicate and aluminum silicate), clay, alumina, talc, titanium oxide, mono-, di- and tri-calcium phosphate, cellulose polymers, and combinations thereof.

Useful softeners and emulsifiers include, e.g., tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof Useful coloring agents including whiteners include, e.g., FD&C-type dyes and lakes, fruit and vegetable extracts, titanium dioxide, and combinations thereof.

The gum base can optionally include wax. An example of a wax-free gum base is disclosed in U.S. Pat. No. 5,286,500, the disclosure of which is incorporated herein by reference.

The water soluble bulk portion can include bulk sweeteners, high intensity sweeteners, flavoring agents, softeners, emulsifiers, colors, acidulants, fillers, antioxidants, and combinations thereof.

Softeners are added to the chewing gum in order to optimize the chewability and mouth feel of the gum. The softeners, which are also known as plasticizers and plasticizing agents, generally constitute from about 0.5% by weight to about 15% by weight of the chewing gum. Suitable softeners include, e.g., glycerin, lecithin, and combinations thereof. Aqueous sweetener solutions such as those containing sorbitol, hydrogenated starch hydrolysates, corn syrup, and combinations thereof, can also be used as softeners and binding agents in chewing gum.

Bulk sweeteners include both sugar and sugarless components. The chewing gum can include from about 5% by weight to about 95% by weight, from about 20% by weight to about 80% by weight, or even from about 30% by weight to about 60% by weight bulk sweetener. Sugar sweeteners generally include saccharide-containing components including, e.g., sucrose, dextrose, maltose, dextrin, dried invert sugar, fructose, levulose, glactose, corn syrup solids, and combinations thereof. Sugarless sweeteners include, e.g., sugar alcohols such as sorbitol, mannitol, xylitol, hydrogenated starch hydrolysates, maltitol, and combinations thereof.

The gum can optionally include artificial sweeteners including, e.g., sucralose, aspartame, N-substituted APM derivatives such as neotame, salts of acesulfame, altitame, saccharin and its salts, cyclamic acid and its salts, glycyrrhizinate, dihydrochalcones, thaumatin, monellin, and combinations thereof. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and sugarless sweeteners may be used in chewing gum. Additionally, the softener may also provide additional sweetness such as with aqueous sugar or alditol solutions.

Useful low calorie bulking agents include, e.g., polydextrose, Raftilose, Raftilin, fructooligosaccharides, palatinose oligosaccharide, guar gum hydrolysate, indigestible dextrin, and combinations thereof.

A variety of flavoring agents can are also suitable including, e.g., essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion. The flavor agent can be present in the gum in amounts of from about 0.1% by weight to about 15% by weight gum, or even from about 0.2% by weight to about 5% by weight.

Useful methods of manufacturing chewing gum base and the chewing gum end product are disclosed in, e.g., U.S. Pat. No. 6,949,264 (McGrew et al.), U.S. Pat. No. 3,995,064 (Ehrgott et al.) and U.S. Pat. No. 4,459,311 (DeTora et al.) U.S. Pat. No. 5,045,325 (Lesko et al.), and. U.S. Pat. No. 4,555,407 (Kramer et al.), U.S. Pat. No. 4,968,511 (D'Amelia et al.), U.S. Pat. Nos. 5,543,160, 5,800,847, 5,397,580, 5,523,097, 5,419,919 and 5,571,543, European Publication No. 0,273, 809 (General Foods France), French Publication No. 2,635, 441 (General Foods France) and incorporated herein.

The invention will now be described by way of the following examples.

EXAMPLES

Test Procedures

Test procedures used in the examples include the following.

Breath Alcohol Content (BAC) Test Method I

An individual inserts the mouthpiece of a ALCOHAWK portable digital breath alcohol content tester (Q3 Innovations, LLC) into his or her mouth and exhales into the device in accordance with the device instructions until a reading appears on the device. The value on the display is recorded in units of % BAC (blood alcohol content).

Example 1

A base effervescent powder formulation is prepared by combining 1000 mg sorbitol powder, 650 mg sodium bicarbonate powder, and 2000 mg dried wild guava leaf extract (boiling water soluble extract), in a plastic bag and shaking the bag until a visually uniform granulation is obtained. All of the ingredients are sieved in a number 12 sieve prior to combining.

To 3650 mg of the base, 1300 mg citric acid, 20 mg sucralose, 20 mg VELTOL ULTRA flavor agent (Danisco, St. Louis Mo.), 130 mg natural orange flavor, 20 mg natural tangerine flavor, 20 mg natural peach flavor, and 20 mg natural grapefruit flavor are added. The ingredients are placed in a plastic bag and shaken until a uniform granulation is obtained as determined by visual observation.

The resulting composition is expected to be a dark brown liquid with sediment on the bottom of the glass.

Example 2

To 3650 mg of the base of Example 1, 1400 mg citric acid, 20 mg sucralose, 20 mg VELTOL ULTRA flavor agent, and 100 mg artificial ice tea flavor are added. The ingredients are placed in a plastic bag and shaken until a uniform granulation is obtained as determined by visual observation.

The granulation of Example 2 is placed in a number of air tight sealed metal foil pouches. The stability of the packaged granulations of Example 2 at room temperature (RT), 40° C. at 75% relative humidity and 45° C. is studied for four weeks and the expected results are set forth in Table 1. No puffing is expected.

TABLE 1

| Example | 1 Week | | | 2 Weeks | | | 3 Weeks | | | 4 Weeks | | |
|---|---|---|---|---|---|---|---|---|---|---|---|---|
| 2 | RT | 40° C. | 45° C. | RT | 40° C. | 45° C. | RT | 40° C. | 45° C. | RT | 40° C. | 45° C. |
| Puffing? | No | No | No | No | No | No | No | No | No | No | No | No |

Example 3

An effervescent tablet is prepared by combining the following ingredients with manual mixing until uniform to form a base: 900 mg sorbitol instant, 850 mg No. 5 sodium bicarbonate, 100 mg sodium carbonate grade 50, and 1000 mg dried wild guava leaf extract (boiling water soluble extract). Each of the ingredients is sieved through a number 12 sieve prior to combining.

To 2850 mg of the base is added 1500 mg citric acid anhydrous fine granular, 30 mg mineral oil, 25 mg sucralose, 150 mg natural orange flavor, 35 mg natural tangerine flavor, 25 mg natural grapefruit flavor, and 15 mg natural peach flavor.

The composition is then formed into tablets using a tablet press to an average mass of 4.64 g, average thickness of 0.261 in and average hardness of 8 kP. The tablets are expected to disintegrate in one minute 40 seconds in room temperature tap water to a black suspension of guava. Some sediment is expected on the bottom of the glass. The taste is expected to be good.

Example 4

To 2850 mg of the base prepared above in Example 3 is added 1500 mg citric acid anhydrous fine granular, 30 mg mineral oil, 25 mg sucralose, 150 mg natural orange flavor, 35 mg natural tangerine flavor, 25 mg natural grapefruit flavor, 15 mg natural peach flavor, and 5 mg FD&C Red food coloring number 40.

The composition is then formed into tablets using a tablet press to an average mass of 4.74 g, average thickness of 0.272 in and average hardness of 7.1 kP. The tablets are expected to disintegrate in two minutes in room temperature tap water to a dispersion having black foam on the surface includes particulate suspended throughout, and a deep red purple color.

Dosing Study

Group I

Each test subject in a first test group consumed a beverage that included an approximately 5 g tablet prepared according the method of Example 4 dissolved in approximately 8 ounces of tap water. The test subjects then consume alcoholic beverages for a period of approximately one hour. Most test subjects consume three or more alcoholic beverages.

After one hour of drinking each test subject is tested according to the Breath Alcohol test method set forth above. The expected results are reported in Table 2.

TABLE 2

| Volunteer | Gender | Age | Height | Weight | BAC Reading |
|---|---|---|---|---|---|
| 1 | M | 25-29 | 5'8-6' | >200 | 0.06 |
| 2 | M | 25-29 | 5'8-6' | >200 | 0.02 |
| 3 | M | 40-49 | 5'8-6' | >200 | 0.05 |
| 4 | M | 30-39 | 5'8-6' | 176-200 | 0.08 |
| 5 | F | 25-29 | 5'3-5'7 | 176-200 | 0.08 |
| 6 | F | 25-29 | 5'8-6' | 151-175 | 0.07 |
| 7 | F | 40-49 | 5'3-5'7 | 136-150 | 0.12 |
| 8 | F | 30-39 | 5'3-5'7 | 136-150 | 0.10 |
| 9 | F | 30-39 | ≦5'2 | 136-150 | 0.06 |
| 10 | F | 25-29 | 5'3-5'7 | 110-135 | 0.06 |

Group II

Each test subject in a second test group consumes alcoholic beverages for a period of approximately one hour. Most test subjects consume three to five alcoholic beverages. Each test subject is tested according to the Breath Alcohol Content test method (the results are identified as BAC Reading 1). Each test subject then consumes a tablet prepared according to Example 4 and then rests for 25 minutes. Each test subject is then tested again according to the Breath Alcohol Content test method (the results are identified as BAC Reading 2). The expected results are reported in Table 3.

Note that test subject 11 consumes 5 drinks and is re-tested twenty minutes after the first test conducted at the original 25 minute interval. His blood alcohol is expected to register a drop from 0.14 to 0.10.

TABLE 3

| Subject | Gender | Age | Height | Weight | No. of Drinks | BAC Reading 1 | BAC Reading 2 |
|---|---|---|---|---|---|---|---|
| 11 | M | 30-39 | 5'8-6' | >200 | 5 | 0.14 | 0.12 |
| 12 | F | 30-39 | 5'8-6' | 176-200 | Unknown | 0.10 | 0.08 |
| 13 | M | 40-49 | 5'8-6' | 176-200 | 4 | 0.15 | 0.09 |
| 14 | M | 40-49 | 5'8-6' | 176-200 | 3 | 0.13 | 0.14 |
| 15 | M | 25-29 | 5'8-6' | 176-200 | 4 | 0.11 | 0.10 |
| 16 | F | 40-49 | 5'3-5'7 | 151-175 | 3 | 0.13 | 0.07 |
| 17 | M | 40-49 | 5'8-6' | 151-175 | 3 | 0.08 | 0.12 |
| 18 | F | 25-28 | 5'3-5'7 | 151-175 | 3 | 0.12 | 0.03 |
| 19 | F | 30-39 | 5'3-5'7 | 136-150 | 5 | 0.16 | 0.10 |

Other embodiments are within the claims.

What is claimed is:

1. A method of using guava extract, the method comprising administering at least 250 mg of a water-soluble extract of dried guava leaves to a human experiencing fatigue.

2. The method of claim 1, wherein the administering comprises administering at least 500 mg of the guava extract to the human.

3. The method of claim 1, wherein said administering comprises administering at least about 1000 mg of the guava extract to the human.

4. The method of claim 1, wherein the administering comprises administering an effervescent tablet comprising
   the guava extract,
   an effervescent couple comprising an acid and a base,
   a binder and
   a lubricant.

5. The method of claim 1, wherein the administering guava extract comprises administering at least 500 mg of the guava extract, the method further comprising administering at least one of taurine, ginseng, and carnitine.

6. The method of claim 5 further comprising administering at least one of glucono-D-lactone, vitamin B12, pyridoxine and thiamine.

7. The method of claim 1, wherein the administering guava extract comprises administering at least about 1000 mg of the guava extract, the method further comprising administering at least one of taurine, ginseng, and carnitine.

8. The method of claim 7 further comprising administering at least one of glucono-D-lactone, vitamin B12, pyridoxine and thiamine.

9. The method of claim 1, wherein the administering guava extract comprises administering at least 500 mg of the guava extract, the method further comprising administering glucono-D-lactone.

10. The method of claim 1, wherein the administering guava extract comprises administering at least about 1000 mg of the guava extract, the method further comprising administering glucono-D-lactone.

* * * * *